United States Patent [19]
Huffman

[11] Patent Number: 5,276,306
[45] Date of Patent: Jan. 4, 1994

[54] HAND-HELD HEATING DEVICE FOR DISLODGING AND REMOVING SKIN-EMBEDDED TICKS AND OTHER ARACHNIDS

[76] Inventor: Robert A. Huffman, W164 N8928 Water Street, Menomonee Falls, Wis. 53051

[21] Appl. No.: 980,668

[22] Filed: Nov. 24, 1992

[51] Int. Cl.⁵ .................. H05B 1/00; A61B 17/50; H01M 1/00; F23C 3/00
[52] U.S. Cl. .................. 219/229; 30/140; 43/144; 126/229; 219/221; 219/227; 219/230; 219/241; 606/28; 606/131; 606/210
[58] Field of Search ............ 219/200, 201, 221, 227, 219/229, 230, 241; 126/229; 606/131, 210, 28; 43/144; 30/140

[56] References Cited

U.S. PATENT DOCUMENTS

| | | |
|---|---|---|
| D. 262,260 | 12/1981 | Meyer et al. |
| D. 285,283 | 8/1986 | Cheng . |
| 1,968,867 | 8/1934 | Angell ................ 606/28 X |
| 2,206,994 | 7/1940 | Zent ................... 219/229 |
| 2,533,947 | 12/1952 | Lipnicki et al. ........ 219/227 X |
| 2,669,642 | 2/1954 | Menges ............... 219/229 X |
| 3,023,748 | 3/1962 | Bruskin .............. 219/227 X |
| 3,364,577 | 1/1968 | Oakleaf et al. ......... 219/229 X |
| 3,651,306 | 3/1972 | Glyptis . |
| 3,707,258 | 12/1972 | Schlitt . |
| 3,980,861 | 9/1976 | Fukunaga ............ 606/28 X |
| 4,213,460 | 7/1980 | Weiner ............... 43/144 X |
| 4,598,855 | 7/1986 | Bell et al. . |
| 4,938,764 | 7/1990 | Glaberson ............ 606/131 |
| 4,976,718 | 12/1990 | Daniell .............. 606/131 |
| 4,979,771 | 12/1990 | Childs ............... 43/144 X |
| 5,002,323 | 3/1991 | Idsund ............... 606/210 |
| 5,078,729 | 1/1992 | Eichorn .............. 606/210 |

FOREIGN PATENT DOCUMENTS 775112 12/1934 France .................. 606/28

OTHER PUBLICATIONS

Brochure regarding cauterizing device by Medical Diagnostic Service, Inc.

*Primary Examiner*—Anthony Bartis
*Attorney, Agent, or Firm*—Nilles & Nilles

[57] ABSTRACT

A device for removing deer ticks and similar insects from a person's skin is disclosed. The device includes a heatable pointed needle and a spoon member located in spaced relationship alongside the needle with the bowl of the spoon facing the needle. The needle is used for poking the tick in order to cause it to retract its stinger and back off of the skin, at which point the tick may be removed in its entirety by scooping it with a spoon member located next to the hot needle. In a first embodiment of the invention, the needle and spoon member are carried on a body unit or base member in the form of a hand held gun, and the needle may be heated by an internal, self-electrical power source and heating element, or by a secondary heat source. In a second embodiment, the needle and spoon are mounted on a base member which may be attached to a flame-type cigarette lighter to heat the needle.

8 Claims, 1 Drawing Sheet

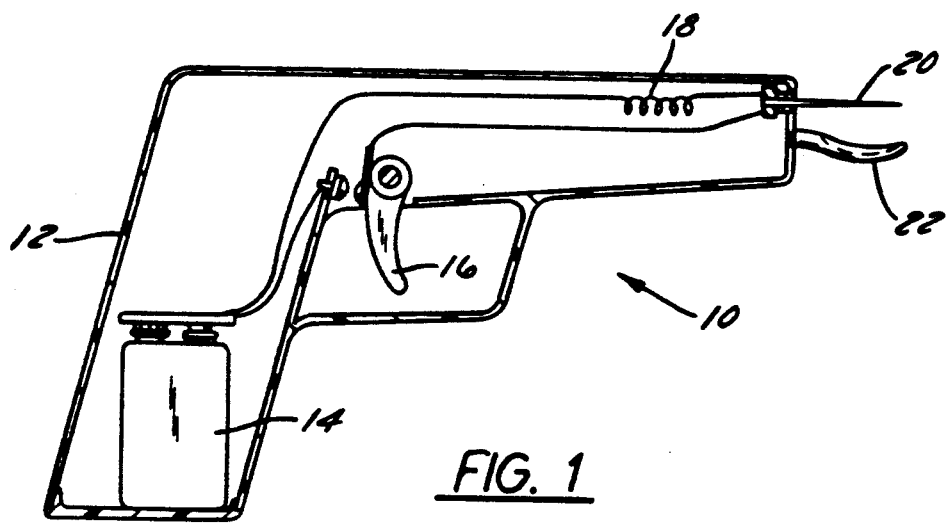
FIG. 1
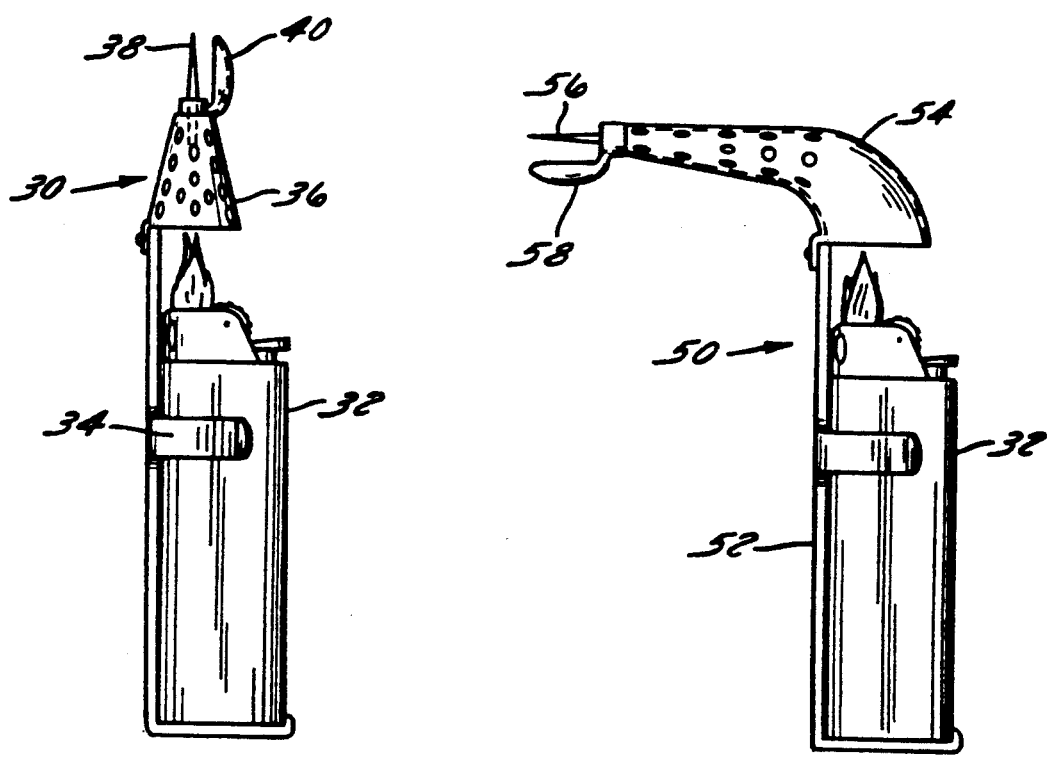
FIG. 2
FIG. 3

HAND-HELD HEATING DEVICE FOR DISLODGING AND REMOVING SKIN-EMBEDDED TICKS AND OTHER ARACHNIDS

BACKGROUND OF THE RELATED ART

This invention relates to a device for removing deer ticks and the like from a person's skin.

Deer ticks are small arachnids (slightly larger than the related mites) which attach themselves to warm blooded vertebrate to feed. These bloodsucking parasitic insects, often found in heavily wooded areas, are carriers of many infectious diseases. A recent increase in the incidence of Lyme's Disease is widely considered to have been caused by the spread of the disease through deer ticks.

Recreational activities such as hiking, fishing, hunting and camping in wooded areas expose a human being to the possibility of a deer tick becoming attached to his or her body. Once on the skin, the deer tick drives its stinger through the skin in order to access the blood flow to feed, thereby providing a path for transmitting diseases carried by the tick. It is therefore imperative that the deer tick be removed before the stinger has full penetrated the skin.

At the end of a day in the woods, a person should check his or her body for the presence of deer ticks. By that time, however, the tick may have imbedded itself in the skin (although the stinger has not yet fully penetrated the skin) so that removal may be difficult. Merely pulling the tick off of the skin with one's finger tips or with a tweezers may result in breaking the body of the tick away from the stinger, leaving the stinger in the skin. One method of effecting complete removal of the tick, both body and stinger, is by lighting a match and then, immediately after extinguishing the flame, placing the hot embers against the tick. The hot match tends to cause the tick to back off of the skin, at that point enabling one to easily remove the tick in its entirety. This method of removing deer ticks, however, is both cumbersome and painful.

SUMMARY OF THE INVENTION

A device for removing deer ticks and similar parasitic insects from a person's skin is disclosed. The invention includes a means for heating a pointed needle for poking the tick to back it off of the skin, and a spooning means for removing the tick in its entirety. The needle and spoon are carried on a hand held body unit or base member, with the needle projecting outward therefrom and the spoon located in spaced relationship alongside the needle with the bowl of the spoon facing the needle.

The device includes a self-contained battery power unit and heating elements, and a means for activating the power unit to heat the pointed needle. Alternatively, the device may be adapted to utilize a secondary heat source, such as a flame-type cigarette lighter, to heat the needle. The device is small, lightweight, and easy to fabricate.

The primary object of the invention is therefore to provide an effective, inexpensive device for removing disease carrying ticks and similar insects from a person's skin. Other objects and advantages of the invention will become apparent from the following description which sets forth, by way of illustration and example, certain preferred embodiments of the invention.

BRIEF DESCRIPTION OF THE DRAWINGS

The drawings, which constitute a part of the specification and include exemplary embodiments of the present invention, include the following:

FIG. 1 is a plan view of a first embodiment of the tick removal device of the present invention which utilizes a self-contained power unit to provide a heat source.

FIG. 2 is a plan view of a second embodiment of the invention which utilizes a secondary heat source.

FIG. 3 is plan view of a third embodiment of the invention which also uses a secondary heat source.

DETAILED DESCRIPTION OF THE INVENTION

A first embodiment of the tick removal device of the present invention is shown in FIG. 1 and designated with reference numeral 10. The device comprises a body unit in the form of a small hand held gun 12, including a handle, barrel and trigger. A heating element or heating coil 18 is located in the barrel of the gun body 12. A self-contained power unit 14, such as a 9 volt battery, held within the handle of the gun body 12 provides a power source for energizing the heating element 18. A trigger mechanism 16 activates the power unit 14.

A pointed needle 20 projects outward from the end of the barrel of the gun body 12. Upon activation of the power unit 14 with the trigger mechanism 16, the heating element 18 is heated thereby also heating the pointed tip of the needle 20. Touching or poking the tick with the pointed tip of the hot needle 20 causes the tick to retract its stinger and back off of the person's skin.

A spoon member 22 also projects outward from the end of the gun barrel. The spoon member 22 is positioned relative to the pointed needle 20 such that, as the tick is poked by the hot needle 20, the curved end of the spoon member 22 may be scooped beneath the tick to remove it from the person's skin.

A second embodiment of the invention is shown in FIG. 2 and designated by reference numeral 30. The second embodiment 30 utilizes a secondary heat source 32 for heating the pointed needle 38. The device includes a base section 34 for mounting it to the head of an ordinary hand held cigarette lighter 32, such as a BIC ® disposable lighter. A tunnel section 36 made of brass or copper captures heat from the flame of the lighter 32. The tunnel section 36 has an open end connected to the base section 34 and a closed end opposite of the open end. The tunnel section 36 is appropriately ventilated to provide adequate air for the flame to burn. The second embodiment 30 likewise includes a pointed needle 38 and a spoon member 40 projecting from the closed end of the tunnel section 36.

The flame from the lighter 32 heats the end of the needle 38. Again, by touching the tick with the pointed end of the needle 38 the tick has a tendency to back off of the person's skin and may then be scooped away by the spoon member 40. On the second embodiment shown in FIG. 2, the tunnel section 36 is substantially straight from end to end.

The third embodiment of the device 50 shown in FIG. 3 also comprises a base section 52, tunnel section 54, needle 56 and spoon member 58, except that the closed end of the tunnel section 54 is turned, in this particular instance turned approximately 90° relative to the open end. Turning the needled end of the tunnel section away from the open flame helps to prevent the pointed needle from becoming too hot and thereby avoiding the risk of burning the person on whom the device is to be used.

The invention disclosed herein is designed as a personnel health and safety device to enable people to quickly and easily eradicate ticks from their bodies. The device is very lightweight, inexpensive, and compact enough to fit in the palm of the hand. The relatively simple construction makes it inexpensive to manufacture, and thereby provides a very effective means for removing ticks without the risk of burns caused by traditional methods of removal.

It is recognized that a number of embodiments of the present invention are disclosed herein. Other embodiments which utilize the essence of the invention may be constructed. Therefore, specific details disclosed above are not to be interpreted as limiting the invention, but are merely a basis of the claims and are instructive for teaching one skilled in the art to variously practice the present invention in any appropriately detailed manner. Changes may be made in details of construction of the invention without departing from the spirit and scope of the invention, especially as defined in the following claims.

I claim as my invention:

1. A tick removal device comprising:
   a body unit in the form of a small hand held gun body;
   a heating element within the body unit;
   a self-contained power unit within the body unit for energizing the heating element;
   a trigger mechanism for activating the power unit;
   a pointed tip in heat exchange relationship with the heating element and projecting outward from the end of the gun barrel of the body unit with the tip being heatable upon activation of the power unit for poking the tick therewith;
   a spoon member projecting outward from the body unit and extending in spaced side-by-side relationship below the pointed tip with the bowl of the spoon member facing the pointed tip for receiving and lifting the tick from a person's skin.

2. The tick removal device according to claim 1, wherein the spoon member has a curved end for spooning it beneath the tick.

3. A device for removing deer ticks and the like from a person's skin comprising:
   a base section mountable onto the head of a hand held flame-type cigarette lighter;
   a tunnel section for capturing the heat of a flame from the lighter, the tunnel section having an open end for receiving the flame from the lighter connected to the base section and a substantially closed end opposite thereof;
   a needle projecting outward from the closed end of the tunnel section in heat exchange relationship therewith for poking the deer tick, the needle being heatable by the flame of the lighter; and
   a spoon member projecting alongside the needle in spaced relationship thereto from the closed end of the tunnel section with the bowl of the spoon member facing the needle for lifting the tick from the person's skin.

4. The device for removing deer ticks according to claim 3, wherein the tunnel section is ventilated to provide sufficient air for the flame of the lighter.

5. The device for removing deer ticks according to claim 3, wherein the tunnel section is substantially straight from end to end.

6. The device for removing deer ticks according to claim 3, wherein the closed end of the tunnel section is turned relative to the open end.

7. The device for removing deer ticks according to claim 3, wherein the end of the spoon member is displaced slightly from the end of the needle such that as the tick is poked by the hot needle the tick has a tendency to back off of the person's skin onto the spoon member.

8. The device for removing deer ticks according to claim 3, wherein the spoon member has a curved end for spooning it beneath the tick.

* * * * *